United States Patent [19]
Archer

[11] Patent Number: 5,609,618
[45] Date of Patent: Mar. 11, 1997

[54] APPARATUS AND METHOD FOR INDUCING FIBRILLATION

[75] Inventor: Stephen T. Archer, Sunnyvale, Calif.

[73] Assignee: Ventritex, Inc., Sunnyvale, Calif.

[21] Appl. No.: 568,036

[22] Filed: Dec. 6, 1995

[51] Int. Cl.⁶ .................................................. A61N 1/32
[52] U.S. Cl. .................................................. 607/74; 607/8
[58] Field of Search .................................. 607/4, 5, 8, 72, 607/74, 75, 76

[56] References Cited

U.S. PATENT DOCUMENTS

| | | | |
|---|---|---|---|
| 3,602,229 | 1/1971 | Jaros | 607/72 |
| 5,129,392 | 7/1992 | Bardy et al. | |
| 5,215,083 | 6/1993 | Drane et al. | |
| 5,279,293 | 1/1994 | Andersen et al. | 607/5 |
| 5,395,373 | 3/1995 | Ayers | 607/8 |
| 5,470,341 | 11/1995 | Kuehn et al. | 607/5 |
| 5,489,293 | 2/1996 | Pless et al. | 607/5 |

FOREIGN PATENT DOCUMENTS

| | | | |
|---|---|---|---|
| 473002 | 3/1992 | European Pat. Off. | 607/8 |
| 589252 | 3/1994 | European Pat. Off. | 607/5 |
| 305892 | 6/1971 | U.S.S.R. | 607/5 |

OTHER PUBLICATIONS

"Digital System for Artificial Fibrillation of Animal Hearts", Schwingshackl, et al., *Biomedical Engineering*, vol. 8, No. 11, Nov. 1973, pp. 472–474.

"Cadence® Tiered therapy Defibrillator System—V–100 Serial Pulse Generator and Programmer", Physician's Manual, Ventritex, Inc., Jan. 1993.

*Primary Examiner*—Jeffrey R. Jastrzab
*Attorney, Agent, or Firm*—Steven M. Mitchell; Mark J. Meltzer

[57] ABSTRACT

A method and apparatus for inducing fibrillation in a patient's heart by delivering an alternating current stimulus to the heart from a DC-to DC converter. The hardware of a conventional implantable cardioverter/defibrillator (ICD) is utilized with a modification to the control algorithms. Particularly, when it is desired to induce fibrillation in a patient's heart, typically during ICD implant defibrillation threshold (DFT) testing, a command is delivered from an external instrument to the ICD to deliver the fibrillation shock. The DC-to-DC converter which is normally used to charge the ICD high voltage capacitors is activated and immediately thereafter a first pair the high voltage output switches of the output stage are closed for about 4 milliseconds. This delivers an initial pulse of one polarity. Following an interval of about 4 milliseconds, a second pair of the high voltage output switches are closed for 4 milliseconds delivering an opposite polarity pulse. The output current from the DC-to-DC converter is provided to the defibrillation electrodes and through the patient's heart. This stimulus of alternating polarity pulses is continued for a predetermined time of between about 30 milliseconds to 5 seconds. At that point all the output switches are opened and the converter is shut off. This stimulus delivered directly to the patient's heart induces fibrillation.

15 Claims, 3 Drawing Sheets

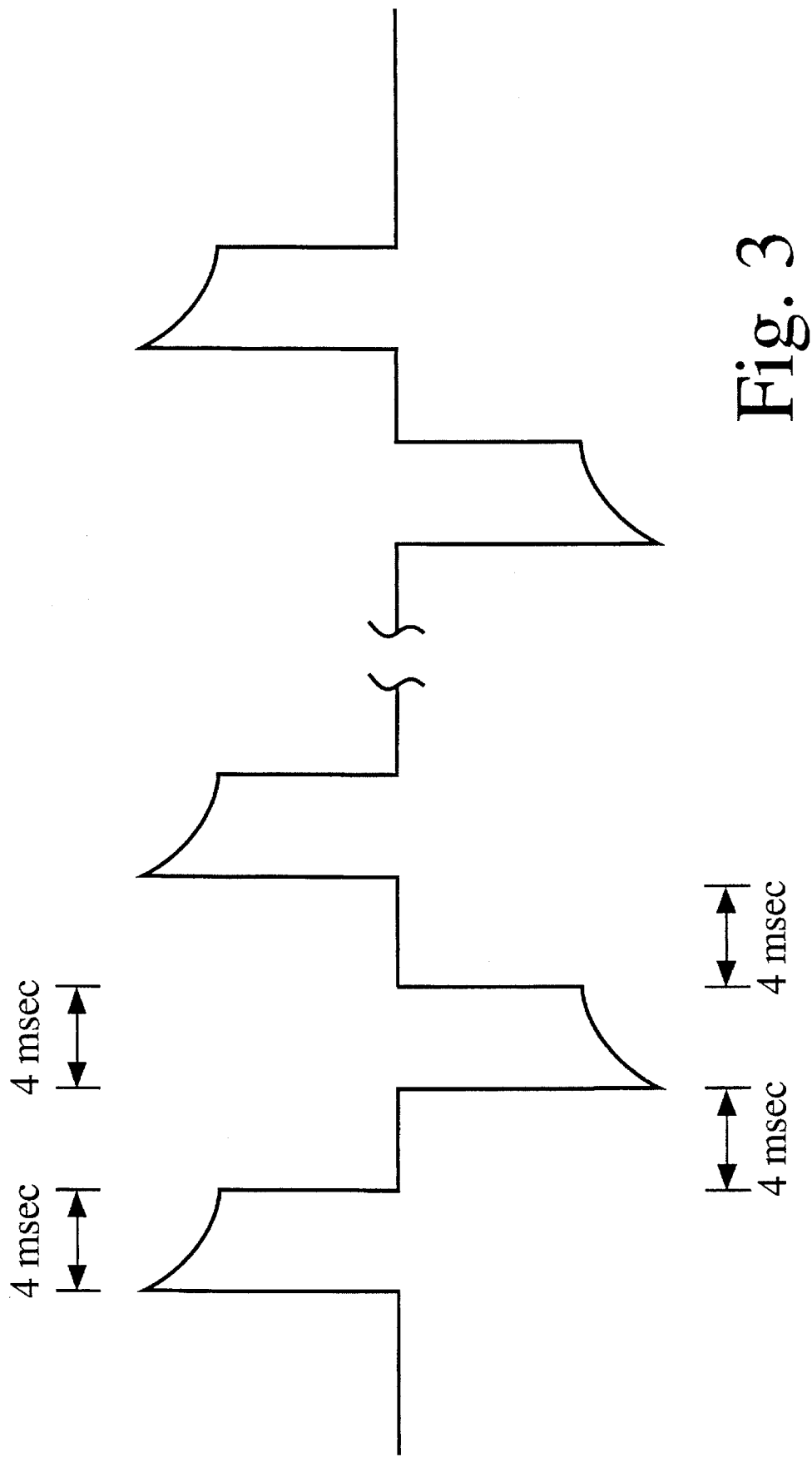

APPARATUS AND METHOD FOR INDUCING FIBRILLATION

BACKGROUND OF THE INVENTION

1. Field of the Invention

The present invention relates generally to medical stimulators and more specifically to implantable cardioverters and defibrillators.

2. Description of the Prior Art

When implanting an implantable defibrillator, it is desirable to test the device's operability to ensure that it is capable of reliably defibrillating the heart. In order to accomplish this, it is necessary to first induce fibrillation in the patient's heart, and then determine whether the implantable defibrillator is capable of terminating the induced fibrillation. Typically, rapid pacing from the implanted defibrillator or an external pulse generator or an external 60 Hz low voltage transformer has been used in inducing fibrillation.

It would be desirable to improve the fibrillation induction function in an implantable defibrillator, to allow for a more fully automated testing regimen and to simplify the implantation procedure. However, incorporation of a true 60 Hz alternating current fibrillator into an implantable device poses substantial technical difficulties.

U.S. Pat. No. 5,129,392 to Bardy et al discloses an automatic fibrillator for inclusion in an implantable defibrillator. Fibrillation is induced using overdrive pacing. The effective refractory period of the patient's heart is measured during pacing. A fibrillation inducing pulse is delivered at a calculated time interval following an overdrive pacing pulse. This approach requires complex tinting calculations and may not be effective in all cases in inducing fibrillation.

U.S. Pat. No. 5,215,083 to Drane et al discloses an apparatus and method for fibrillation induction. At least a portion of a pulse train of "micro-shocks" delivered from the high voltage capacitors are synchronized to the patient's T-waves. The length of the series of trains and the microshock pulse widths are programmable parameters and the polarity of the shocks may be alternated within a train. This technique is also complex and may not be consistently effective.

Copending U.S. patent application Ser. No. 08/568,044, filed Dec. 6, 1995, to Fain et al. and assigned to the assignee of the present application discloses a method and apparatus for inducing fibrillation in a patient's heart by delivering a direct current shock to the heart from a DC-to-DC converter. The hardware of a conventional implantable cardioverter/ defibrillator (ICD) is utilized with a modification to the control algorithms. The DC-to-DC converter which is normally used to charge the ICD high voltage capacitors is activated and immediately thereafter or following a short period to allow the high voltage capacitors to charge, the high voltage output switches of the output stage are closed. This delivers the output current from the DC-to-DC converter to the defibrillation electrodes and through the patient's heart. This pulse or shock is continued for a predetermined time of between about 30 milliseconds to 5 seconds. At that point the output switches are opened and the converter is shut off. This DC stimulus delivered directly to the patient's heart induces fibrillation. A problem with this system is that the voltage available from the output of the DC-to-DC converter may not be sufficiently high to consistently induce fibrillation.

It is therefore an object of the invention to provide an improved method and apparatus for inducing fibrillation in a patient's heart.

SUMMARY OF THE INVENTION

The present invention provides a method and apparatus for inducing fibrillation in a patient's heart by delivering a sequence of alternating polarity pulses to the heart. In a preferred embodiment of the invention, the hardware of a conventional implantable cardioverter/defibrillator (ICD) is utilized with a modification to the control algorithms. Particularly, when it is desired to induce fibrillation in a patient's heart, typically during ICD implant defibrillation threshold (DFT) testing, a command is delivered from an external instrument to the ICD to deliver the plurality of pulses to induce fibrillation. The fibrillation inducing stimulus may have the first pulse in the sequence either R-wave synchronous or asynchronous. To initiate a stimulus using the DC-to-DC converter, which comprises a step-up transformer normally used to charge the ICD high voltage capacitors, the converter is activated. Immediately thereafter or following a short period to synchronize with an R-wave, the high voltage output switches of the ICD output stage which are configured to deliver both positive and negative pulses of a biphasic waveform are alternately actuated to deliver a positive pulse, no output, a negative pulse and no output and then this sequence is repeated for a programmed time period. This delivers an output waveform which is essentially a 60 Hz alternating current to the defibrillation electrodes and through the patient's heart. The approximately 60 Hz current is achieved by having a duty cycle of about 4 milliseconds (4 msec for each pulse and 4 msec for each off period). Because the duty cycle is less than 100%, a higher output voltage is available from the DC-to-DC converter than if the converter is coupled directly to the heart. The defibrillation electrodes are those known in the art, preferably transvenous lead defibrillation electrodes or epicardial patch electrodes. The fibrillation inducing stimulus is continued for a predetermined time of between about 30 milliseconds to 5 seconds. At that point all the output switches are opened and the converter is shut off. This stimulus delivered directly to the patient's heart induces fibrillation. Fibrillation induction is of course followed by the ICD detecting the fibrillation and delivering a programmed defibrillation shock to rescue the patient.

BRIEF DESCRIPTION OF THE DRAWINGS

The various features and advantages of the present invention may be more readily understood with reference to the following detailed description taken in conjunction with the accompanying drawings in which:

FIG. 3 is a representation of the fibrillation inducing output waveform.

DETAILED DESCRIPTION OF THE INVENTION

Figure 1:
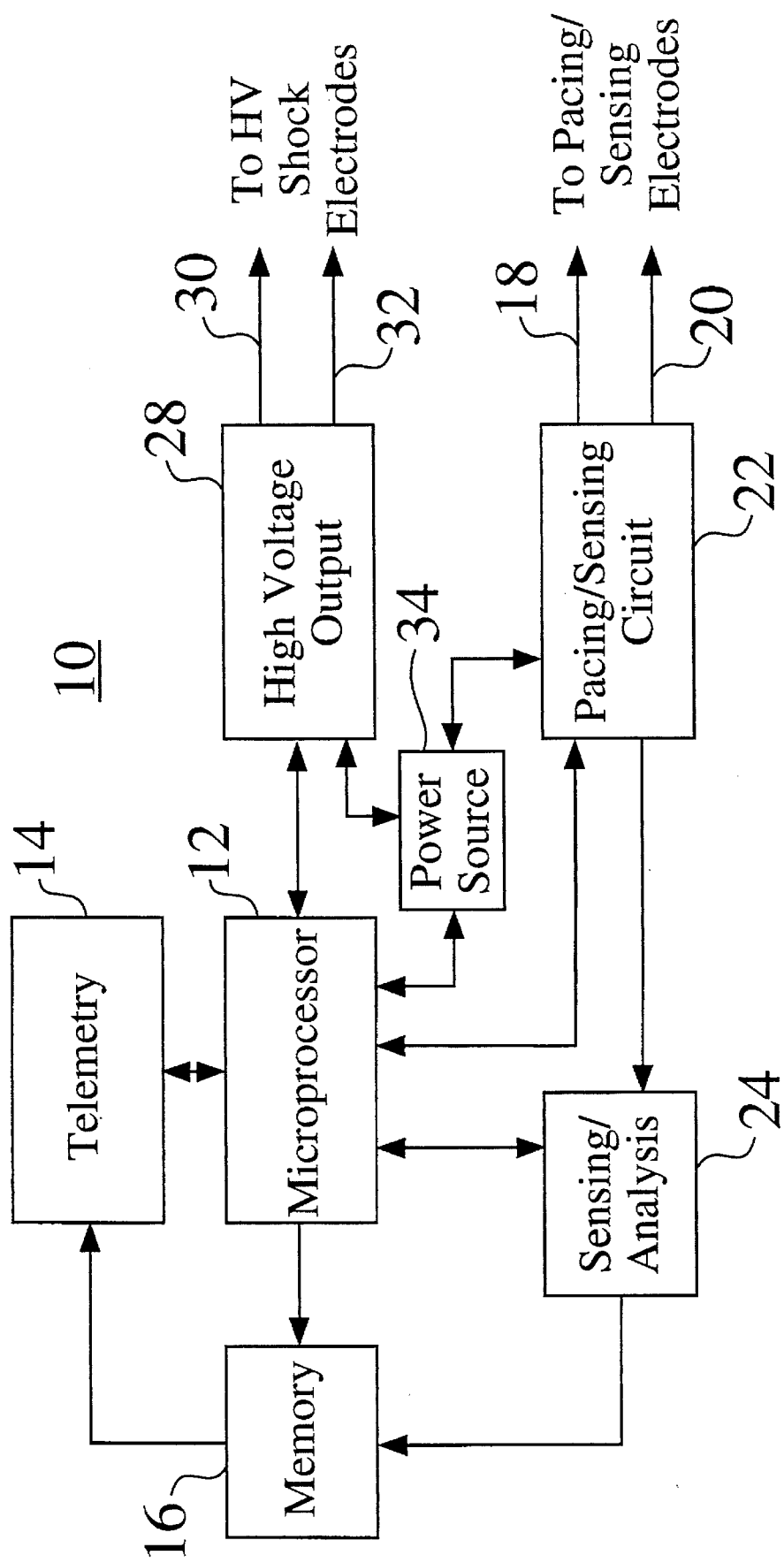
FIG. 1 is a block diagram of an implantable cardioverter/ defibrillator according the invention.

The invention will now be discussed with reference to FIG. 1 which is a block diagram of an implantable cardioverter/defibrillator (ICD) 10. The method of the invention can be practiced with the currently designed ICDs such as the one described in U.S. Pat. No. 5,111,816 to Pless et al., which patent is incorporated herein by reference. The apparatus of the invention simply requires modification of the control algorithms of the ICD.

ICD 10 includes a microprocessor 12 which controls the primary functions of the ICD. Control could alternatively be achieved with a state machine. The microprocessor 12 communicates with an external programmer (not shown) through a telemetry section 14. Commands from the programmer through telemetry section 14 to microprocessor 12 are used to send commands to the ICD including fibrillation induction. Telemetry section 14 can also be used to transmit stored electrograms and other device information from a memory section 16 to the programmer, as is well known in the art.

Sensing of electrograms from a patient's heart is achieved through a pair of sensing conductors 18, 20 coupled on one end to sensing electrodes (not shown) proximate the patient's heart and on the other end to a pacing/sensing circuit 22. Sensed electrograms are provided to a sensing/analysis circuit 24 which communicates with and is controlled by microprocessor 12.

In a preferred embodiment of the invention, ICD 10 can provide a number of different therapies to the patient's heart in response to detected arrhythmias including bradycardia pacing, antitachycardia pacing, cardioversion and defibrillation shocks. Pacing is provided under control of microprocessor 12 by a pacing/sensing circuit 22 and conductors 18, 20. High voltage cardioversion and defibrillation shocks are provided under control of microprocessor 12 by high voltage output circuit 28 which will be discussed in more detail with reference to FIG. 2 below. The high voltage shocks are provided between a pair of terminals coupled to conductors 30, 32. These conductors are coupled to at least a pair of high voltage electrodes (not shown). There are numerous pacing/sensing electrode and high voltage electrode configurations known in the art, any of which could be used in practice of the present invention. These include bipolar, integrated bipolar and unipolar sensing configurations and high voltage electrodes including a right ventricular defibrillation electrode, superior vena cava defibrillation electrode, a subcutaneous patch electrode, a defibrillator can electrode and others.

ICD 10 further includes a power source 34 which provides power to the various circuits of the device. The power source is one or more low voltage, high current batteries, for example a lithium silver vanadium oxide battery.

Figure 2:
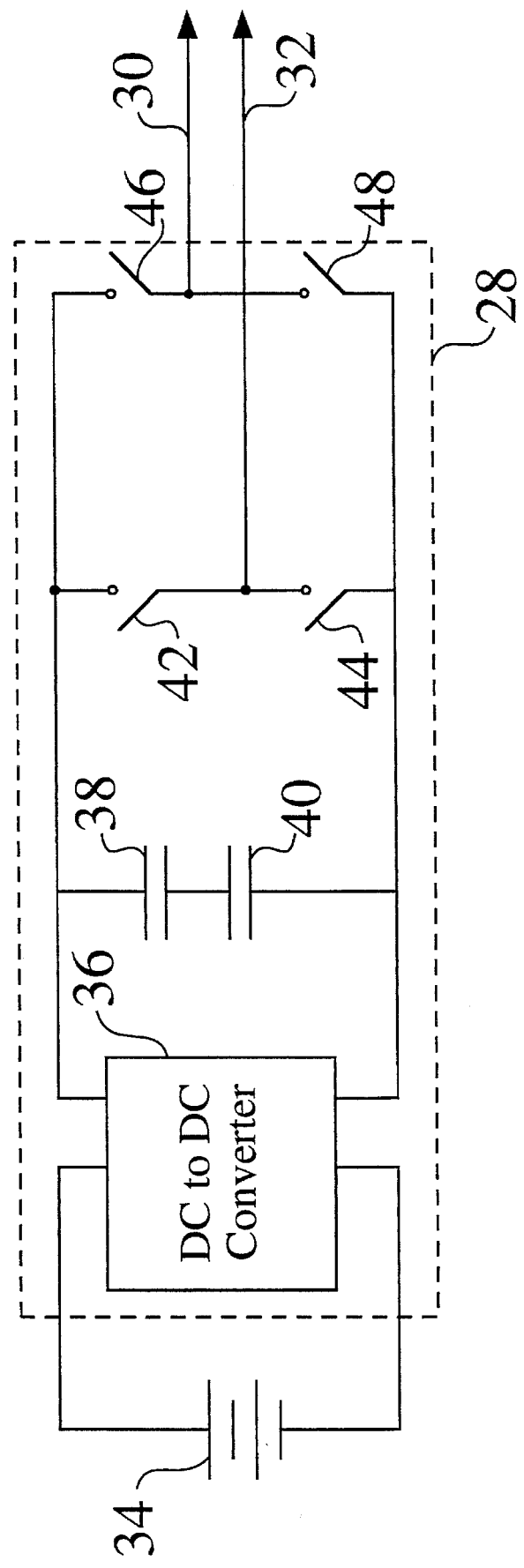
FIG. 2 is a schematic diagram of the high voltage output stage of the invention.

Referring now to FIG. 2, the power source 34 and high voltage output circuit 28 of ICD 10 are shown. Battery 34 is coupled to a DC-to-DC converter 36 of the type well known in the art. Such a DC-to-DC converter is disclosed in U.S. Pat. Nos. 4,257,087 and 4,186,437 to Cuk which patents are hereby incorporated by reference. The principal component of DC-to-DC converter 36 is a step-up flyback transformer which is used to charge a pair of series connected high voltage capacitors 38, 40. One or more capacitors could be used but two series connected aluminum electrolytic capacitors are typically used.

Output circuit 28 further includes an H-bridge circuit including switches 42, 44, 46 and 48 which are under control of microprocessor 12. The H-bridge circuit is provided to allow the delivery of biphasic cardioversion and defibrillation shocks to the patient's heart. With the H-bridge circuit shown in FIG. 2, the pulse from DC-to-DC converter 36 are provided to the patient's heart with alternating polarity by selectively closing switches 42 and 48 together, then opening all the switches, closing switches 44 and 46 together and then again opening all the switches. This output waveform is illustrated in FIG. 3. To achieve an approximately 60 Hz output, each pulse is 4 msec and the pulses are separated from each other by 4 msec intervals. This results in a 62.5 Hz output.

In an alternative embodiment of the invention, each of the pulses is of the same polarity. In this embodiment, the pulses are 8 msec each separated by 8 msec intervals.

The method of the invention will now be described. The invention is typically used at the time an ICD is being implanted to assist in performing defibrillation threshold (DFT) testing. In this procedure, a stimulus is delivered to the patient's heart to induce fibrillation and the ICD being implanted is allowed to detect the fibrillation and deliver a defibrillation shock. Using the ICD to provide the fibrillation inducing stimulus as well as the defibrillation shock simplifies the DFT testing procedure. It is also useful for follow-up testing to avoid surgery to place an additional catheter for fibrillation induction. When the implanting physician is ready to induce fibrillation, a command is sent from the external programmer (not shown) through telemetry section 14 to microprocessor 12. The fibrillation inducing stimulus from DC-to-DC converter 36 can be delivered with the first pulse either synchronous with a sensed R-wave or asynchronously. If the DC stimulus is to be delivered synchronously, stimulus delivery is delayed until the next sensed R-wave.

Microprocessor 12 issues controlling commands to deliver the stimulus. The DC-to-DC converter 36 is actuated by repetitively coupling battery 34 to the transformer coil in the converter. A first pair of switches 42, 48 in high voltage output circuit 28 are then closed directly coupling the output of DC-to-DC converter 36 to the patient's heart through conductors 30, 32 and the defibrillation electrodes for a specified period which is 4 msec in the preferred embodiment. All output switches are then opened for 4 msec. The second pair of switches 44, 46 are then closed coupling the output of DC-to-DC converter 36 to the patient's heart in the opposite polarity through conductors 30, 32 and the defibrillation electrodes, again for a period of 4 msec. All output switches are then again opened for 4 msec. This alternation of opposite polarity pulses using output switches 42, 44, 46, 48 continues for a period between about 0.03 to 5 seconds. This period is more preferably between about 0.3 and 3 seconds. The period may be programmed by the physician using the external programmer.

It should be understood that various alternatives to the embodiments of the invention described herein may be employed in practicing the invention. For example, the pulse widths and inter-pulse intervals can be modified. It is thus intended that the following claims define the scope of the invention and that structures and methods within the scope of these claims and their equivalents be covered thereby.

What is claimed is:

1. A method of inducing fibrillation in a patient's heart using an implantable pulse generator, comprising:

activating a DC-to-DC converter in said pulse generator; and coupling a series of alternating polarity pulses directly from said DC-to-DC converter to said patient's heart to deliver a fibrillation inducing stimulus.

2. The method of claim 1 wherein said coupling step includes alternately closing a first pair and a second pair of output switches in an output stage of said implantable pulse generator.

3. The method of claim 1 wherein each of said opposite polarity pulses is coupled to said patient's heart for about 4 milliseconds with an interval between said pulses of about 4 milliseconds to generate an alternating current having an approximately 60 Hz frequency.

4. The method of claim 1 wherein said alternating pulses are delivered for a time period of between 0.03 and 5 seconds.

5. The method of claim 1 and further including the step of sensing an electrogram signal from said patient's heart and delivering a first pulse of said fibrillation inducing stimulus to said patient's heart synchronous with a sensed R wave.

6. The method of claim 1 and further including the step of delivering a command from an external control device to initiate delivery of said fibrillation inducing stimulus.

7. An automatic fibrillator for inducing fibrillation in a patient's heart, comprising:

a DC-to-DC converter;

a plurality of output switches coupled between an output of said DC-to-DC converter and at least a pair of therapy delivery electrodes; and a controller for activating said DC-to-DC converter and closing said switches to couple a sequence of opposite polarity pulses from said DC-to-DC converter through said switches to said patient's heart.

8. The fibrillator of claim 7 wherein said controller is adapted to couple said DC-to-DC converter to said patient's heart for a predetermined time of between 0.03 and 5 seconds.

9. The fibrillator of claim 7 and further including high voltage capacitor means coupled to said DC-to-DC converter in parallel with said output switches.

10. The fibrillator of claim 7 and wherein said plurality of switches comprises an H-bridge circuit of a high voltage output stage.

11. An implantable pulse generator for inducing fibrillation in a patient's heart comprising:

pulse generation means including a DC-to-DC converter for providing an output;

means for activating said DC-to-DC converter; and means for coupling the output of said DC-to-DC converter directly to said patient's heart as a sequence of pulses to induce fibrillation in said patient's heart.

12. The pulse generator of claim 11, said means for coupling including:

a high voltage output stage having two pairs of high voltage output switches; and means for alternately closing opening said pairs of high voltage output switches.

13. The pulse generator of claim 11 and further including means for deactivating said DC-to-DC converter following a predetermined time period.

14. The pulse generator of claim 11 and further including means for sensing an electrogram signal from said patient's heart and means for delivering said fibrillation inducing shock to said patient's heart synchronous with a sensed R wave.

15. The pulse generator of claim 11 and further including means for receiving a command from an external control device to initiate delivery of a fibrillation inducing stimulus.

\* \* \* \* \*